(12) United States Patent
Hakoshima

(10) Patent No.: US 11,266,307 B2
(45) Date of Patent: Mar. 8, 2022

(54) EVALUATION DEVICE, EVALUATION METHOD, AND NON-TRANSITORY STORAGE MEDIUM

(71) Applicant: JVC KENWOOD Corporation, Yokohama (JP)

(72) Inventor: Shuji Hakoshima, Yokohama (JP)

(73) Assignee: JVC KENWOOD Corporation, Yokohama (JP)

( * ) Notice: Subject to any disclaimer, the term of this patent is extended or adjusted under 35 U.S.C. 154(b) by 366 days.

(21) Appl. No.: 16/270,615

(22) Filed: Feb. 8, 2019

(65) Prior Publication Data
US 2019/0261849 A1 Aug. 29, 2019

(30) Foreign Application Priority Data

Feb. 28, 2018 (JP) .............................. JP2018-034850

(51) Int. Cl.
*A61B 3/02* (2006.01)
*A61B 3/032* (2006.01)
*A61B 3/113* (2006.01)
*A61B 3/00* (2006.01)
*A61B 3/14* (2006.01)

(52) U.S. Cl.
CPC ............ *A61B 3/032* (2013.01); *A61B 3/0025* (2013.01); *A61B 3/0041* (2013.01); *A61B 3/0091* (2013.01); *A61B 3/113* (2013.01); *A61B 3/14* (2013.01)

(58) Field of Classification Search
CPC ....... A61B 3/032; A61B 3/113; A61B 3/0041; A61B 3/14; A61B 3/0025; A61B 3/0091; A61B 3/024

USPC ......... 359/209, 237, 239; 351/209, 237, 239
See application file for complete search history.

(56) References Cited

U.S. PATENT DOCUMENTS

2017/0049316 A1* 2/2017 Donaldson ............ A61B 3/024
2017/0245753 A1* 8/2017 Donaldson ............ A61B 3/113
2017/0360295 A1* 12/2017 Oz ....................... G06K 9/3233
2020/0329959 A1* 10/2020 Goldberg ............. A61B 3/0033

FOREIGN PATENT DOCUMENTS

JP 2011-161122 8/2011
JP 2011161122 A * 8/2011

* cited by examiner

*Primary Examiner* — Mahidere S Sahle
(74) *Attorney, Agent, or Firm* — Amin, Turocy & Watson, LLP

(57) ABSTRACT

An evaluation device includes a display screen; a gaze point detection unit that detects a position of a gaze point of an examinee; an area setting unit that sets a specific area for a first indicator on the display screen; a determination unit that determines whether the gaze point is present in the specific area based on the position thereof; a display controller that displays a second indicator at a different position from the first indicator when determining that the gaze point is present in the specific area; a arithmetic unit that determines whether the examinee has recognized the second indicator; and an evaluation unit that evaluates a visual function of the examinee based on a determination result from the arithmetic unit. The display controller doesn't display the second indicator when determining that the gaze point isn't present in the specific area after the second indicator has been displayed.

4 Claims, 12 Drawing Sheets

EVALUATION DEVICE, EVALUATION METHOD, AND NON-TRANSITORY STORAGE MEDIUM

CROSS-REFERENCE TO RELATED APPLICATION

This application claims priority from Japanese Application No. 2018-034850, filed on Feb. 28, 2018, the contents of which are incorporated by reference herein in its entirety.

FIELD

The present application relates to an evaluation device, an evaluation method, and a non-transitory storage medium.

BACKGROUND

As an evaluation method of evaluating whether or not there is a visual field deficiency in a retina, for example, a method of causing an examinee to gaze at a point and examining whether the examinee has recognized an indicator presented around the point is known (for example, Japanese Laid-open Patent Publication No. 2011-161122 A).

In the method disclosed in Japanese Laid-open Patent Publication No. 2011-161122 A, a configuration in which an indicator is presented only when an examinee gazes at a presented indicator is not employed. Accordingly, it is difficult to determine whether an examinee can recognize an indicator with peripheral vision and it is also difficult to accurately evaluate whether or not there is a visual field deficiency. Accordingly, there is demand for a technique capable of performing evaluation with higher accuracy.

SUMMARY

An evaluation device, an evaluation method, and a non-transitory storage medium are disclosed.

According to one aspect, there is provided an evaluation device comprising: a display screen configured to display images; a gaze point detection unit configured to detect a position of a gaze point of an examinee who observes the display screen; an area setting unit configured to set a specific area in an area corresponding to a first indicator which is displayed or disposed on the display screen; a determination unit configured to determine whether the gaze point is present in the specific area based on a detection result of the position of the gaze point; a display controller configured to display a second indicator at a position different from the first indicator on the display screen when the determination unit determines that the gaze point is present in the specific area; a arithmetic unit configured to determine whether the examinee has recognized the second indicator; and an evaluation unit configured to evaluate a visual function of the examinee based on a determination result from the arithmetic unit, wherein the display controller is further configured not to display the second indicator when the determination unit determines that the gaze point is not present in the specific area after the second indicator has been displayed on the display screen.

According to one aspect, there is provided an evaluation method comprising: detecting a position of a gaze point of an examinee who observes a display screen that displays an image; setting a specific area in an area corresponding to a first indicator which is displayed or disposed on the display screen; determining whether the gaze point is present in the specific area based on a detection result of the position of the gaze point; displaying a second indicator at a position different from the first indicator on the display screen when determining that the gaze point is present in the specific area; determining whether the examinee has recognized the second indicator; evaluating a visual function of the examinee based on a determination result of the recognition of the second indicator, and not displaying the second indicator when determining that the gaze point is not present in the specific area after the second indicator has been displayed on the display screen.

According to one aspect, there is provided a non-transitory storage medium that stores an evaluation program causing a computer to perform: detecting a position of a gaze point of an examinee who observes a display screen that displays an image; setting a specific area in an area corresponding to a first indicator which is displayed or disposed on the display screen; determining whether the gaze point is present in the specific area based on a detection result of the position of the gaze point; displaying a second indicator at a position different from the first indicator on the display screen when determining that the gaze point is present in the specific area; determining whether the examinee has recognized the second indicator; evaluating a visual function of the examinee based on a determination result of the recognition of the second indicator, and not displaying the second indicator when determining that the gaze point is not present in the specific area after the second indicator has been displayed on the display screen.

The above and other objects, features, advantages and technical and industrial significance of this application will be better understood by reading the following detailed description of presently preferred embodiments of the application, when considered in connection with the accompanying drawings.

DETAILED DESCRIPTION OF THE PREFERRED EMBODIMENTS

Hereinafter, embodiments of an evaluation device, an evaluation method, and a non-transitory storage medium according to the application will be described with reference to the accompanying drawings. Incidentally, the application is not limited to the embodiments. Further, elements in the following embodiments include elements which can be easily replaced by those skilled in the art or substantially the same elements.

In the following description, a three-dimensional global coordinate system is set and positional relationships between the elements are described therein. A direction which is parallel to a first axis of a predetermined plane is defined as an X-axis direction, a direction which is parallel to a second axis of the predetermined plane perpendicular to the first axis is defined as a Y-axis direction, and a direction which is parallel to a third axis perpendicular to the first axis and the second axis is defined as a Z-axis direction. The predetermined plane includes an XY plane.

Line-of-Sight Detecting Device

Figure 1:
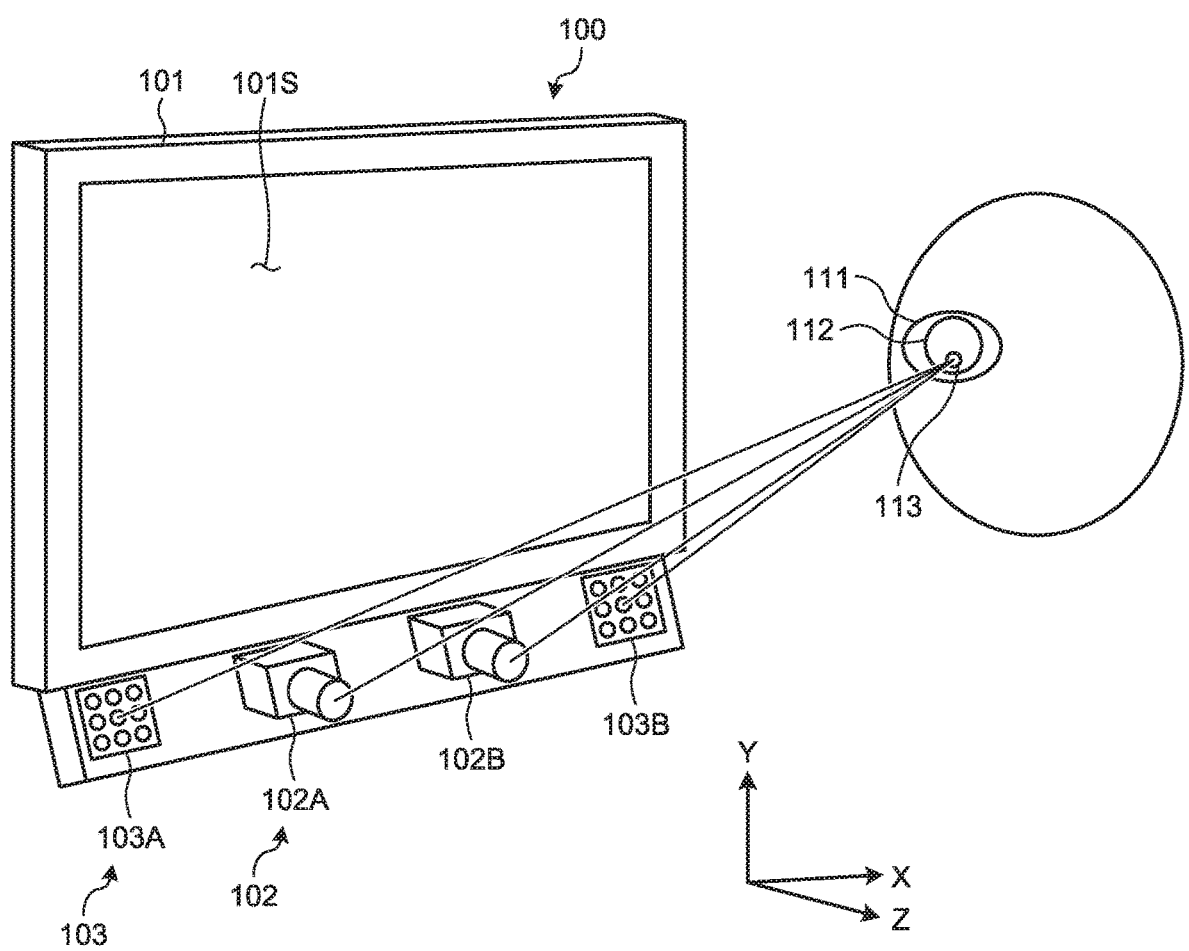
FIG. 1 is a perspective view schematically illustrating an example of a line-of-sight detecting device according to a present embodiment.

FIG. 1 is a perspective view schematically illustrating an example of a line-of-sight detecting device 100 according to a first embodiment. The line-of-sight detecting device 100 is used as an evaluation device that evaluates whether or not there is a visual field deficiency due to glaucoma or the like as a visual function of an examinee. As illustrated in FIG. 1, the line-of-sight detecting device 100 includes a display device 101, a stereo camera device 102, an illumination device 103, and an examinee input unit 70.

The display device 101 includes a flat panel display such as a liquid crystal display (LCD) or an organic electroluminescence (EL) display (OLED). In the present embodiment, the display device 101 includes a display screen 101S. The display screen 101S displays an image. In the present embodiment, the display screen 101S displays, for example, a first indicator and a second indicator for evaluating a visual function of an examinee. The display screen 101S is substantially parallel to the XY plane. The X-axis direction is a horizontal direction of the display screen 101S, the Y-axis direction is a vertical direction of the display screen 101S, and the Z-axis direction is a depth direction which is perpendicular to the display screen 101S.

The stereo camera device 102 includes a first camera 102A and a second camera 102B. The stereo camera device 102 is disposed below the display screen 101S of the display device 101. The first camera 102A and the second camera 102B are disposed in the X-axis direction. The first camera 102A is disposed on the −X side with respect to the second camera 102B. Each of the first camera 102A and the second camera 102B includes an infrared camera and includes, for example, an optical system that can transmit near-infrared light with a wavelength of 850 [nm] and an imaging element that can receive the infrared light.

The illumination device 103 includes a first light source 103A and a second light source 103B. The illumination device 103 is disposed below the display screen 101S of the display device 101. The first light source 103A and the second light source 103B are disposed in the X-axis direction. The first light source 103A is disposed on the −X side with respect to the first camera 102A. The second light source 103B is disposed on the +X side with respect to the second camera 102B. Each of the first light source 103A and the second light source 103B includes a light emitting diode (LED) as the light source and can emit, for example, near-infrared light with a wavelength of 850 [nm]. Incidentally, the first light source 103A and the second light source 103B may be disposed between the first camera 102A and the second camera 102B.

The illumination device 103 emits near-infrared light which is detection light and illuminates an eyeball 111 of an examinee. The stereo camera device 102 images the eyeball 111 with the second camera 102B when the detection light emitted from the first light source 103A is applied to the eyeball 111, and images the eyeball 111 with the first camera 102A when the detection light emitted from the second light source 103B is applied to the eyeball 111.

A frame synchronization signal is output from at least one of the first camera 102A and the second camera 102B. The first light source 103A and the second light source 103B emit detection light based on the frame synchronization signal. The first camera 102A acquires image data of the eyeball 111 when the detection light emitted from the second light source 103B is applied to the eyeball 111. The second camera 102B acquires image data of the eyeball 111 when the detection light emitted from the first light source 103A is applied to the eyeball 111.

When the detection light is applied to the eyeball 111, a part of the detection light is reflected by a pupil 112 and the reflected light from the pupil 112 is incident on the stereo camera device 102. Further, when the detection light is applied to the eyeball 111, a corneal reflex image 113 which is a virtual image of the cornea is formed in the eyeball 111 and light from the corneal reflex image 113 is incident on the stereo camera device 102.

By appropriately setting relative positions between the first camera 102A, the second camera 102B, the first light source 103A, and the second light source 103B, intensity of the light incident on the stereo camera device 102 from the pupil 112 decreases and intensity of the light incident on the stereo camera device 102 from the corneal reflex image 113 increases. That is, an image of the pupil 112 acquired by the stereo camera device 102 has low luminance and an image of the corneal reflex image 113 has high luminance. The stereo camera device 102 can detect the position of the pupil 112 and the position of the corneal reflex image 113 based on the luminance of the acquired image.

Figure 2:
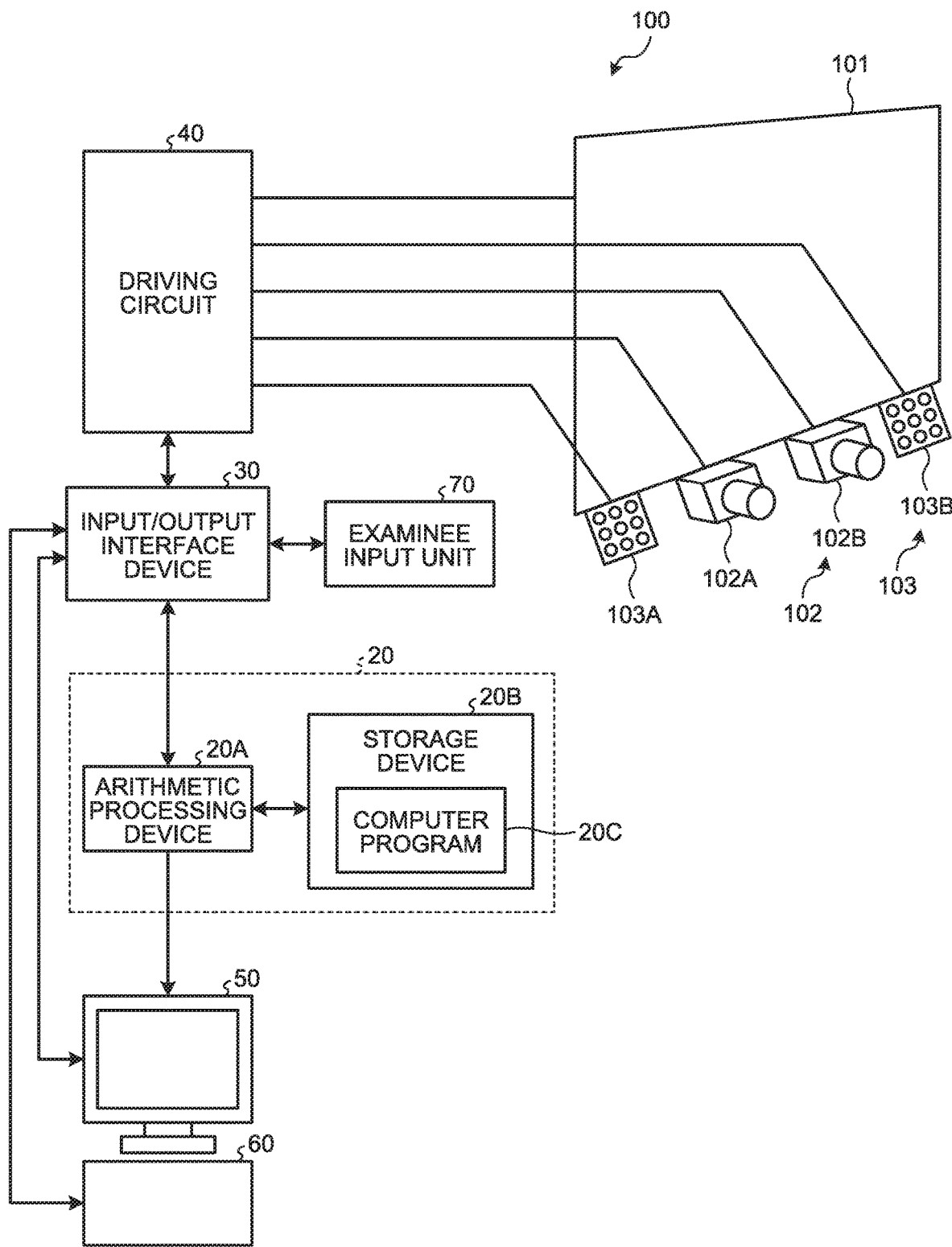
FIG. 2 is a diagram illustrating an example of a hardware configuration of the line-of-sight detecting device according to the embodiment.

FIG. 2 is a diagram illustrating an example of a hardware configuration of the line-of-sight detecting device 100 according to the present embodiment. As illustrated in FIG. 2, the line-of-sight detecting device 100 includes the display device 101, the stereo camera device 102, the illumination device 103, a computer system 20, an input/output interface device 30, a driving circuit 40, an output device 50, an input device 60, and the examinee input unit 70.

The computer system 20, the driving circuit 40, the output device 50, the input device 60, and the examinee input unit 70 perform data communication with each other via the input/output interface device 30. The computer system 20 includes an arithmetic processing device 20A and a storage device 20B. The arithmetic processing device 20A includes a microprocessor such as a central processing unit (CPU). The storage device 20B includes a memory or a storage such as a read only memory (ROM) and a random access memory (RAM). The arithmetic processing device 20A performs an arithmetic process in accordance with a computer program 20C stored in the storage device 20B.

The driving circuit 40 generates drive signals and outputs the drive signals to the display device 101, the stereo camera device 102, and the illumination device 103. Further, the driving circuit 40 supplies image data of the eyeball 111 acquired by the stereo camera device 102 to the computer system 20 via the input/output interface device 30.

The output device 50 includes a display device such as a flat panel display. Incidentally, the output device 50 may include a printer. The input device 60 generates input data by being operated. The input device 60 includes a keyboard or a mouse for a computer system. Incidentally, the input device 60 may include a touch sensor which is disposed on the display screen of the output device 50 which is the display device. The examinee input unit 70 inputs information indicating whether an examinee can recognize an indicator (a second indicator M2) which will be described later. For example, a button switch is used as the examinee input unit 70. In this configuration, for example, when the examinee determines that the examinee can recognize the second indicator M2, an input signal is transmitted to the computer system 20 by causing the examinee to push a button.

In the present embodiment, the display device 101 and the computer system 20 are separate devices. Incidentally, the display device 101 and the computer system 20 may be integrated. For example, when the line-of-sight detecting device 100 includes a tablet personal computer, the computer system 20, the input/output interface device 30, the driving circuit 40, and the display device 101 may be mounted in the tablet personal computer.

Figure 3:
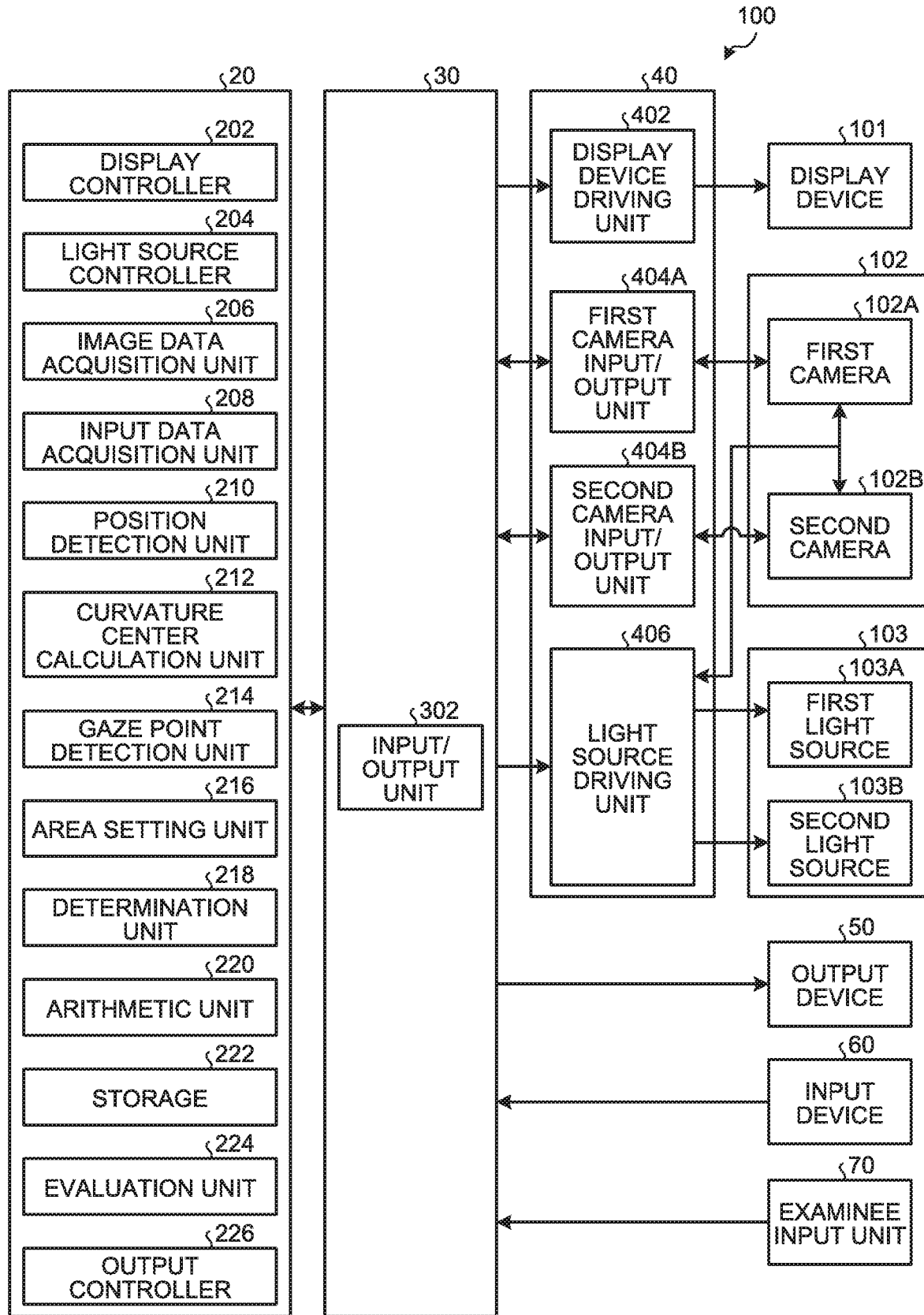
FIG. 3 is a functional block diagram illustrating an example of the line-of-sight detecting device according to the embodiment.

FIG. 3 is a functional block diagram illustrating an example of the line-of-sight detecting device 100 according to the present embodiment. As illustrated in FIG. 3, the input/output interface device 30 includes an input/output unit 302. The driving circuit 40 includes a display device driving unit 402 that generates a drive signal for driving the display device 101 and outputs the drive signal to the display device 101, a first camera input/output unit 404A that generates a drive signal for driving the first camera 102A and outputs the drive signal to the first camera 102A, a second camera input/output unit 404B that generates a drive signal for driving the second camera 102B and outputs the drive signal to the second camera 102B, and a light source driving unit 406 that generates a drive signal for driving the first light source 103A and the second light source 103B and outputs the drive signal to the first light source 103A and the second light source 103B. Further, the first camera input/output unit 404A supplies image data of the eyeball 111 acquired by the first camera 102A to the computer system 20 via the input/output unit 302. The second camera input/output unit 404B supplies image data of the eyeball 111 acquired by the second camera 102B to the computer system 20 via the input/output unit 302.

The computer system 20 controls the line-of-sight detecting device 100. The computer system 20 includes a display controller 202, a light source controller 204, an image data acquisition unit 206, an input data acquisition unit 208, a position detection unit 210, a curvature center calculation unit 212, a gaze point detection unit 214, an area setting unit 216, a determination unit 218, a arithmetic unit 220, a storage 222, an evaluation unit 224, and an output controller 226. The function of the computer system 20 is exhibited by the arithmetic processing device 20A and the storage device 20B.

The display controller 202 displays a first indicator and a second indicator for evaluating a visual function of an examinee on the display screen 101S. The first indicator is an indicator at which an examinee is made to gaze. The second indicator is an indicator that is displayed at a position different from the first indicator on the display screen 101S. The display controller 202 can display the second indicator at multiple different positions. When an indicator corresponding to the first indicator is separately disposed on the display screen 101S, the display controller 202 can omit the display of the first indicator. The second indicator is an indicator which is used to determine whether the examinee has recognized the second indicator with peripheral vision of the retina in a state in which the examinee is gazing at the first indicator. When a determination unit 218 which will be described later determines that the gaze point is present in the specific area, the display controller 202 displays the second indicator at a position different from the first indicator on the display screen. Further, when the determination unit 218 which will be described later determines that the gaze point is not present in the specific area, the display controller 202 does not display the second indicator on the display screen.

The light source controller 204 controls the light source driving unit 406 to control operating states of the first light source 103A and the second light source 103B. The light source controller 204 controls the first light source 103A and the second light source 103B such that the first light source 103A and the second light source 103B emit detection light at different timing.

The image data acquisition unit 206 acquires image data of the eyeball 111 of the examinee acquired by the stereo camera device 102 including the first camera 102A and the second camera 102B from the stereo camera device 102 via the input/output unit 302.

The input data acquisition unit 208 acquires input data generated by the input device 60 being operated from the input device 60 via the input/output unit 302.

The position detection unit 210 detects position data of a pupil center based on the image data of the eyeball 111 acquired by the image data acquisition unit 206. Further, the position detection unit 210 detects position data of a corneal reflection center based on the image data of the eyeball 111 acquired by the image data acquisition unit 206. The pupil center is a center of the pupil 112. The corneal reflection center is a center of the corneal reflex image 113. The position detection unit 210 detects the position data of the pupil center and position data of the corneal reflection center for each of the right and left eyeballs 111 of the examinee.

The curvature center calculation unit 212 calculates position data of the corneal curvature center of the eyeball 111 based on the image data of the eyeball 111 acquired by the image data acquisition unit 206.

The gaze point detection unit 214 detects position data of a gaze point of the examinee based on the image data of the eyeball 111 acquired by the image data acquisition unit 206. In the present embodiment, the position data of the gaze point refers to position data of an intersection between a line-of-sight vector of the examinee which is defined in the three-dimensional global coordinate system and the display screen 101S of the display device 101. The gaze point detection unit 214 detects the line-of-sight vector of each of the right and left eyeballs 111 of the examinee based on the position data of the pupil center acquired by the image data of the eyeball 111 and the position data of the corneal curvature center. After the line-of-sight vector has been detected, the gaze point detection unit 214 detects the position data of the gaze point indicating the intersection between the line-of-sight vector and the display screen 101S.

The area setting unit 216 sets a specific area in a part of the display screen 101S of the display device 101 in which the first indicator is displayed or disposed.

When the specific area is set on the display screen 101S, the determination unit 218 determines whether the gaze point is present in the specific area based on the position data which is the detection result of the position of the gaze point and outputs determination data. The determination unit 218 determines whether the gaze point is present in the specific area, for example, at constant time intervals. The constant time interval can be set to, for example, a period of the frame synchronization signal (for example, every 50 [msec]) output from the first camera 102A and the second camera 102B.

The arithmetic unit 220 includes a timer that detects a time elapsed after the first indicator has been displayed on the display screen 101S. The arithmetic unit 220 determines whether the examinee has recognized the second indicator. The arithmetic unit 220 determines whether the examinee has recognized the second indicator based on an input result from the examinee input unit 70. In the present embodiment, when the input result from the examinee input unit 70 has been detected, the arithmetic unit 220 determines that the examinee has recognized the second indicator. When the input result from the examinee input unit 70 has not been detected, the arithmetic unit 220 determines that the examinee has not recognized the second indicator. The arithmetic unit 220 outputs the determination results.

The evaluation unit 224 evaluates a visual function of the examinee and acquires evaluation data. The evaluation data is data for evaluating the visual function of the examinee based on the determination results from the arithmetic unit 220.

The storage 222 stores image data of images which are displayed on the display screen 101S, the determination data output from the determination unit 218, and the evaluation data output from the evaluation unit 224. The images which are displayed on the display screen 101S includes a still image and a moving image. The storage 222 stores multiple pieces of the image data. The storage 222 stores timing data of start and end of displaying the image data. The storage 222 stores data of the position of the second indicator which is displayed on the display screen 101S. The data of the position of the second indicator may be stored, for example, in correlation with vision of the retina. The storage 222 stores the determination results from the arithmetic unit 220 about whether the examinee has recognized the second indicator in correlation with each of the positions of the second indicator.

The storage 222 stores an evaluation program causing a computer to perform a process of detecting the position of the gaze point of the examinee who observes the display screen on which the image is displayed, a process of setting the specific area in an area corresponding to the first indicator which is displayed or disposed on the display screen, a process of determining whether the gaze point is present in the specific area based on the detection result of the position of the gaze point, a process of displaying the second indicator at a position different from the first indicator on the display screen when the determination unit determines that the gaze point is present in the specific area, a process of determining whether the examinee has recognized the second indicator, and a process of evaluating the visual function of the examinee based on the detection results from the detection unit.

The output controller 226 outputs data to at least one of the display device 101 and the output device 50.

Figure 4:
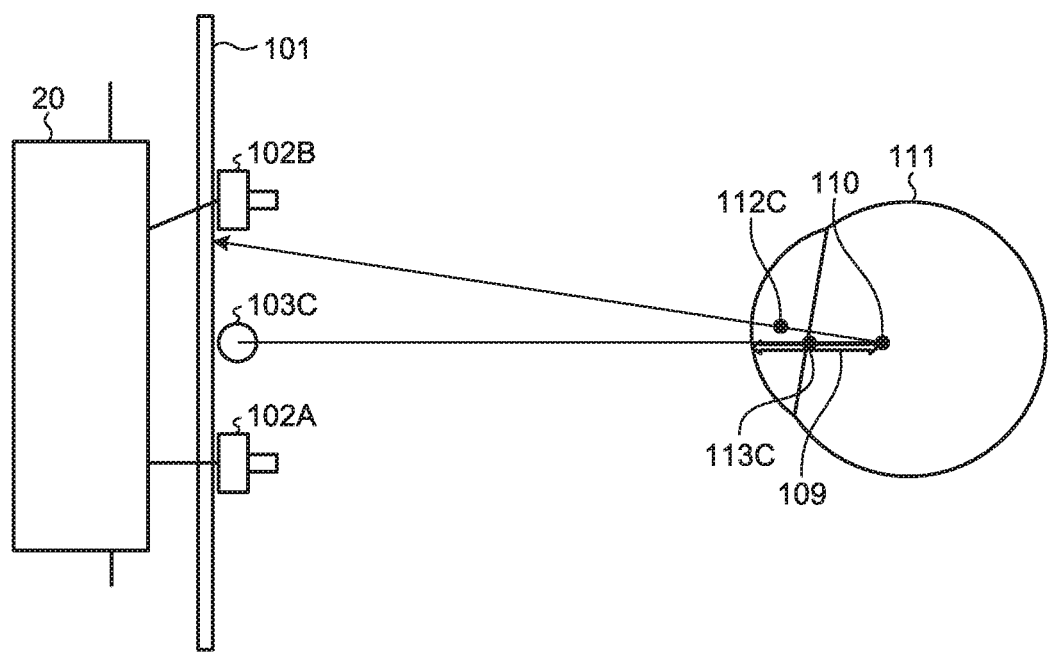
FIG. 4 is a diagram schematically describing a method of calculating position data of a corneal curvature center according to the embodiment.
Figure 5:
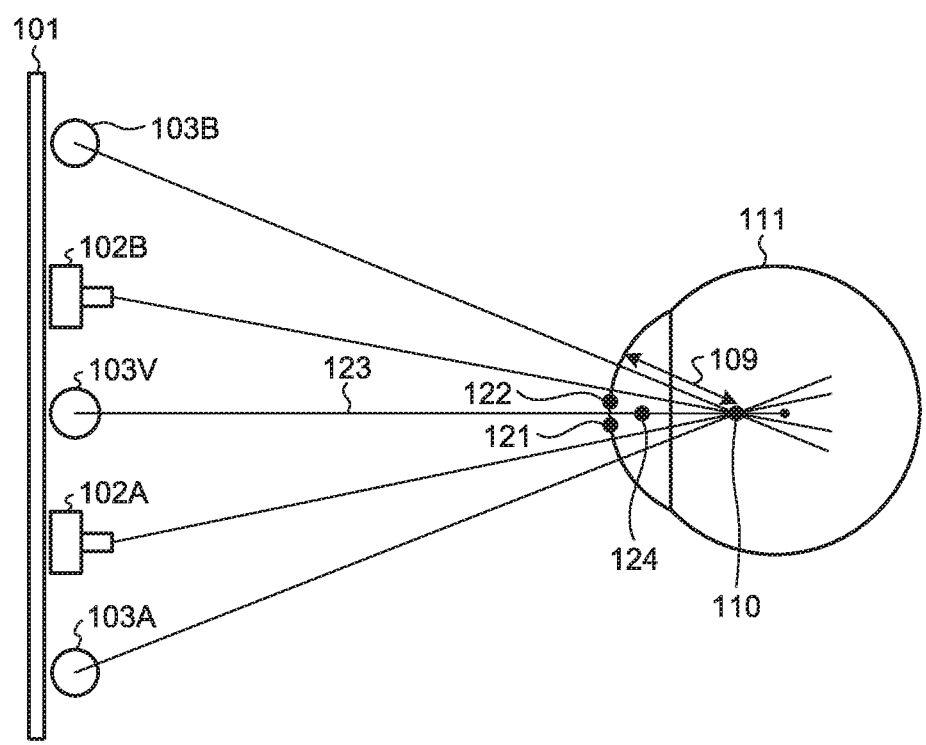
FIG. 5 is a diagram schematically describing a method of calculating position data of the corneal curvature center according to the embodiment.

Next, outline of a process of the curvature center calculation unit 212 according to the present embodiment will be described below. The curvature center calculation unit 212 calculates position data of the corneal curvature center of the eyeball 111 based on the image data of the eyeball 111. FIGS. 4 and 5 are diagrams schematically illustrating a method of calculating the position data of the corneal curvature center 110 according to the present embodiment. FIG. 4 illustrates an example in which the eyeball 111 is illuminated with one light source 103C. FIG. 5 illustrates an example in which the eyeball 111 is illuminated with the first light source 103A and the second light source 103B.

First, the example illustrated in FIG. 4 will be described. The light source 103C is disposed between the first camera 102A and the second camera 102B. A pupil center 112C is a center of the pupil 112. A corneal reflection center 113C is a center of the corneal reflex image 113. In FIG. 4, the pupil center 112C indicates the pupil center when the eyeball 111 is illuminated with one light source 103C. The corneal reflection center 113C indicates the corneal reflection center when the eyeball 111 is illuminated with one light source 103C. The corneal reflection center 113C is present on a straight line that connects the light source 103C to the corneal curvature center 110. The corneal reflection center 113C is positioned at a midpoint between a corneal surface and the corneal curvature center 110. A corneal curvature radius 109 is a distance between the corneal surface and the corneal curvature center 110. Position data of the corneal reflection center 113C is detected by the stereo camera device 102. The corneal curvature center 110 is present on a straight line that connects the light source 103C to the corneal reflection center 113C. The curvature center calculation unit 212 calculates position data at which a distance from the corneal reflection center 113C on the straight line corresponds to a predetermined value as position data of the corneal curvature center 110. The predetermined value is a value which is determined in advance from a general curvature radius value of the cornea and is stored in the storage 222.

Next, the example illustrated in FIG. 5 will be described. In the present embodiment, the first camera 102A, the second light source 103B, the second camera 102B, and the first light source 103A are disposed at positions which are symmetric with respect to a straight line passing through the middle position between the first camera 102A and the second camera 102B. A virtual light source 103V can be considered to be present at the middle position between the first camera 102A and the second camera 102B. A corneal reflection center 121 indicates a corneal reflection center in an image obtained by imaging the eyeball 111 with the second camera 102B. A corneal reflection center 122 indicates a corneal reflection center in an image obtained by imaging the eyeball 111 with the first camera 102A. A corneal reflection center 124 indicates the corneal reflection center corresponding to the virtual light source 103V. Position data of the corneal reflection center 124 is calculated based on position data of the corneal reflection center 121 and position data of the corneal reflection center 122 which are acquired by the stereo camera device 102. The stereo camera device 102 detects the position data of the corneal reflection center 121 and the position data of the corneal reflection center 122 in a three-dimensional local coordinate system which is defined in the stereo camera device 102. Camera calibration based on a stereo calibration method is performed in advance on the stereo camera device 102, and a conversion parameter for converting three-dimensional local coordinate system of the stereo camera device 102 into three-dimensional global coordinate system is calculated. The conversion parameter is stored in the storage 222. The curvature center calculation unit 212 converts the position data of the corneal reflection center 121 and the position data of the corneal reflection center 122 which are acquired by the stereo camera device 102 into position data in the three-dimensional global coordinate system using the conversion parameter. The curvature center calculation unit 212 calculates position data of the corneal reflection center 124 in the three-dimensional global coordinate system based on the position data of the corneal reflection center 121 and the position data of the corneal reflection center 122 which are defined in the three-dimensional global coordinate system. The corneal curvature center 110 is present on a straight line 123 that connects the virtual light source 103V to the corneal reflection center 124. The curvature center calculation unit 212 calculates position data in which a distance from the corneal reflection center 124 on the straight line 123 corresponds to a predetermined value as position data of the corneal curvature center 110. The predetermined value is a value which is determined in advance from a general curvature radius value of the cornea and is stored in the storage 222.

In this way, when there are two light sources, the corneal curvature center 110 is calculated using the same method as the method when there is one light source.

The corneal curvature radius 109 is a distance between the corneal surface and the corneal curvature center 110. Accordingly, the corneal curvature radius 109 is calculated by calculating the position data of the corneal surface and the position data of the corneal curvature center 110.

Figure 6:
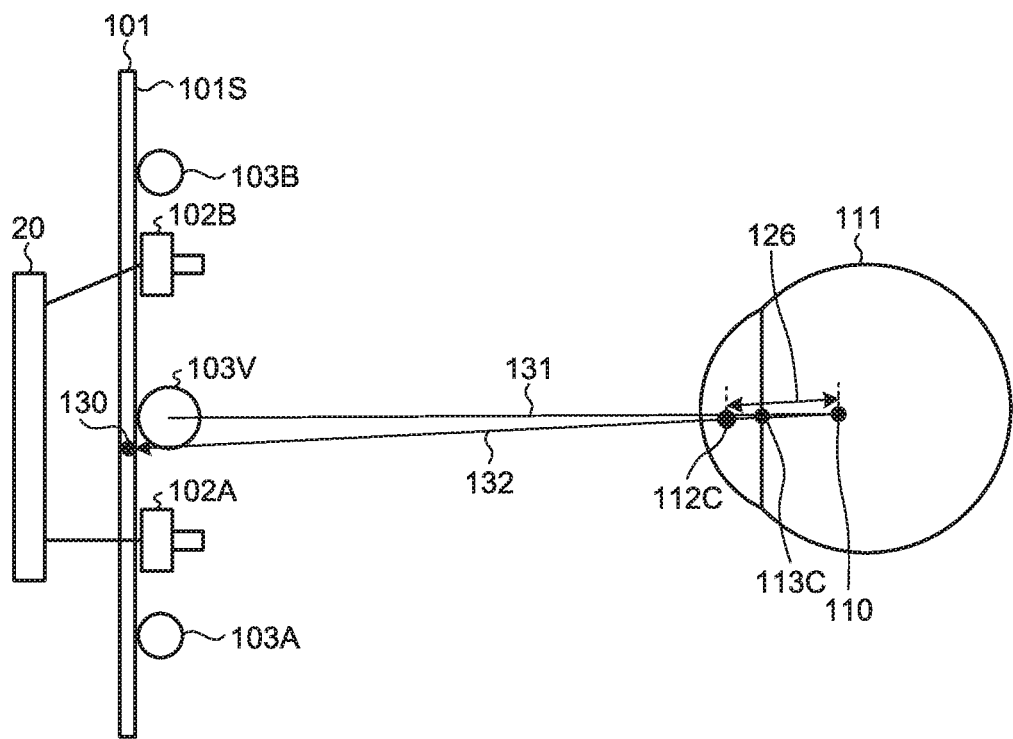
FIG. 6 is a diagram schematically describing an example of a calibration process according to the embodiment.

An example of a line-of-sight detecting method according to the present embodiment will be described below. FIG. 6 is a diagram schematically illustrating an example of a calibration process according to the present embodiment. In the calibration process, a target position 130 is set to cause the examinee to gaze at the target position. The target position 130 is defined in the three-dimensional global coordinate system. In the present embodiment, the target position 130 is set, for example, at a central position of the display screen 101S of the display device 101. Incidentally, the target position 130 may be set at an end position of the display screen 101S. The output controller 226 displays a target image at the set target position 130. A straight line 131 is a straight line that connects the virtual light source 103V to the corneal reflection center 113C. A straight line 132 is a straight line that connects the target position 130 to the pupil center 112C. The corneal curvature center 110 is an intersection between the straight line 131 and the straight line 132. The curvature center calculation unit 212 can calculate the position data of the corneal curvature center 110 based on the position data of the virtual light source 103V, the position data of the target position 130, the position data of the pupil center 112C, and the position data of the corneal reflection center 113C.

Figure 7:
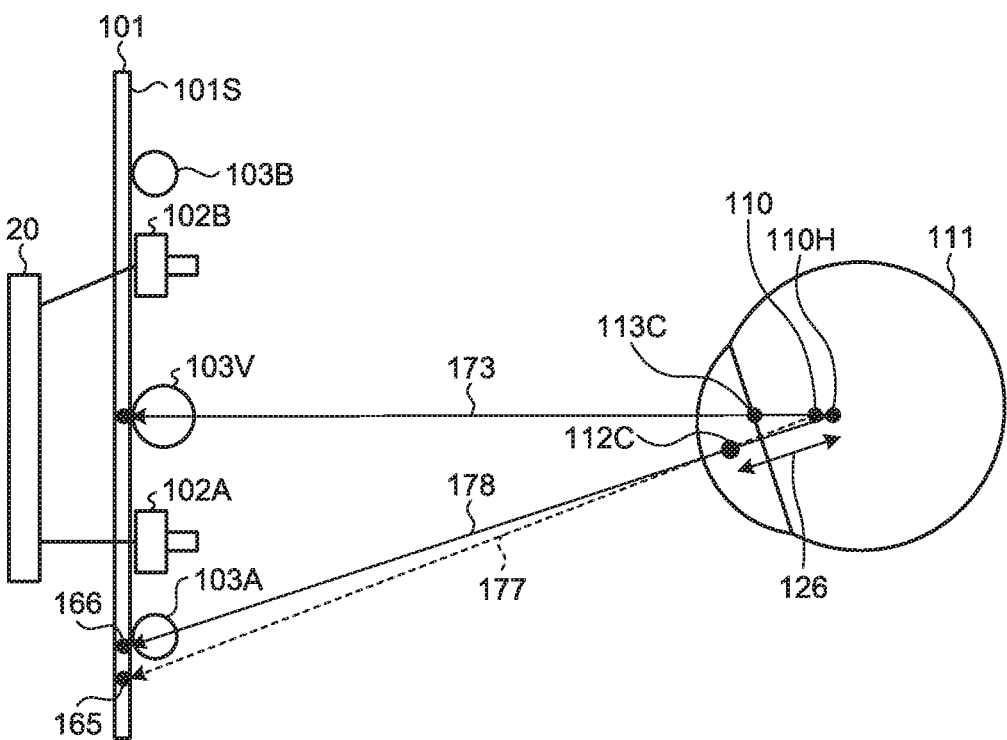
FIG. 7 is a diagram schematically describing an example of a gaze point detecting process according to the embodiment.

A gaze point detecting process will be described below. The gaze point detecting process is performed after the calibration process. The gaze point detection unit 214 calculates a line-of-sight vector of the examinee and position data of the gaze point based on image data of an eyeball 111. FIG. 7 is a diagram schematically illustrating an example of the gaze point detecting process according to the present embodiment. In FIG. 7, the gaze point 165 is a gaze point calculated from the corneal curvature center calculated using a general curvature radius value. A gaze point 166 is a gaze point which is calculated from the corneal curvature center calculated using a distance 126 calculated in the calibration process. The pupil center 112C is a pupil center which is calculated in the calibration process, and the corneal reflection center 113C is a corneal reflection center which is calculated in the calibration process. A straight line 173 is a straight line that connects the virtual light source 103V to the corneal reflection center 113C. The corneal curvature center 110 indicates a position of the corneal curvature center which is calculated from the general curvature radius value. The distance 126 is a distance between the pupil center 112C calculated in the calibration process and the corneal curvature center 110. A corneal curvature center 110H indicates a position of the corrected corneal curvature center which is obtained by correcting the corneal curvature center 110 using the distance 126. The corneal curvature center 110H is calculated based on the facts that the corneal curvature center 110 is located on the straight line 173 and the distance between the pupil center 112C and the corneal curvature center 110 is the distance 126. Accordingly, a line-of-sight 177 which is calculated when using the general curvature radius value is corrected to a line-of-sight 178. Further, the gaze point on the display screen 101S of the display device 101 is corrected from the gaze point 165 to a gaze point 166.

[Evaluation Method]

An evaluation method according to the present embodiment will be described below. In the evaluation method according to the present embodiment, whether or not there is a visual field deficiency due to glaucoma or the like is evaluated as a visual function of the examinee using the line-of-sight detecting device 100.

Figure 8:
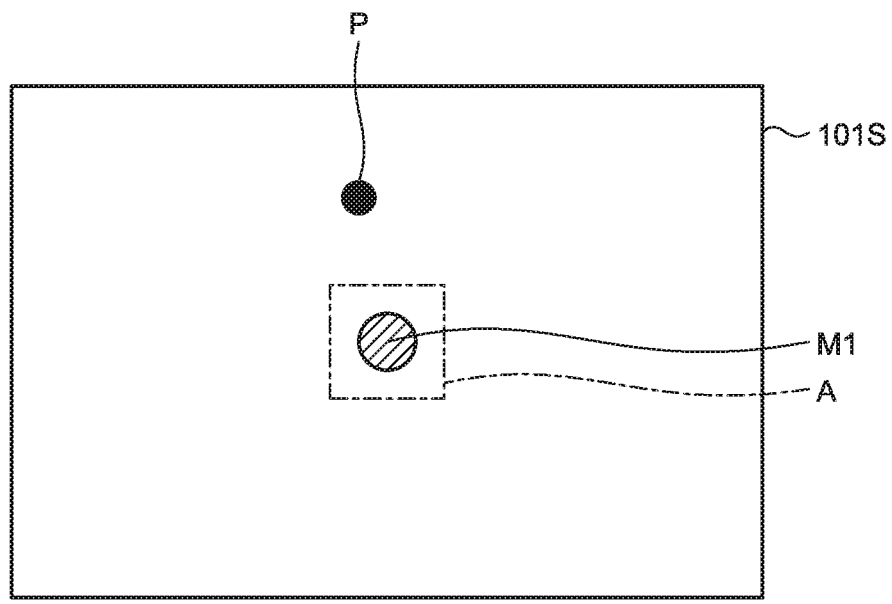
FIG. 8 is a diagram illustrating an example of an indicator which is displayed on a display screen.
Figure 9:
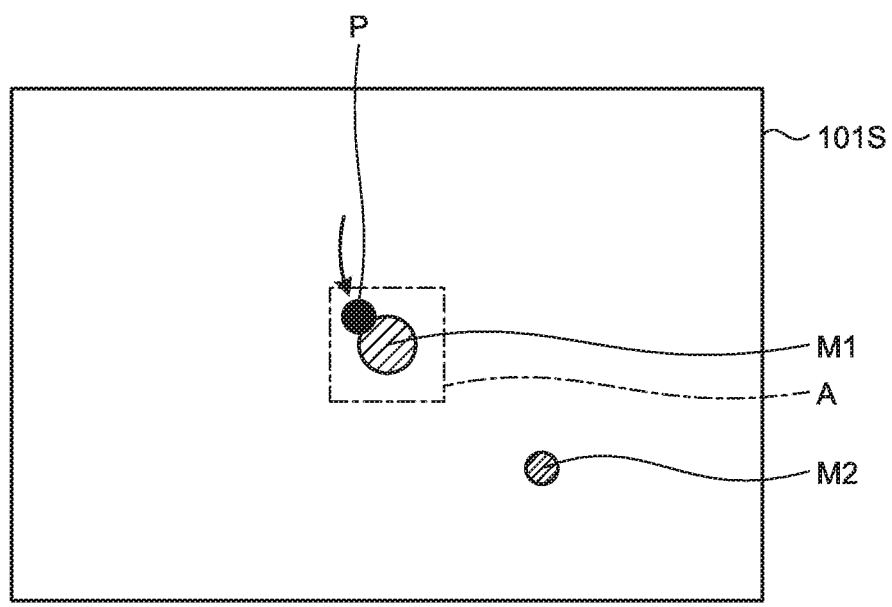
FIG. 9 is a diagram illustrating an example of the indicators which are displayed on the display screen.

FIGS. 8 and 9 are diagrams illustrating an examples of indicators which are displayed on the display screen 101S. As illustrated in FIG. 8, the display controller 202 displays the first indicator M1 at the center of the display screen 101S. The first indicator M1 is an indicator at which the examinee is caused to gaze. The first indicator M1 illustrated in FIG. 8 has, for example, a circular shape, but the application is not limited thereto and may have a different shape.

In FIG. 8, an example of a gaze point P which is displayed as a measurement result on the display screen 101S is illustrated, but the gaze point P is not actually displayed on the display screen 101S. The same applies to the gaze points P in the subsequent drawings. Detection of position data of the gaze point is performed, for example, in a period of a frame synchronization signal (for example, every 50 [msec]) output from the first camera 102A and the second camera 102B. The first camera 102A and the second camera 102B synchronously capture images.

When the first indicator M1 is displayed on the display screen 101S, the area setting unit 216 sets a specific area A corresponding to the first indicator M1. For example, in the example illustrated in FIG. 8, the area setting unit 216 sets the specific area A in a rectangular area surrounding the first indicator M1. The shape of the specific area A is not limited to a rectangle and may be another shape such a circle, an ellipse, or a polygon.

When the first indicator M1 is displayed on the display screen 101S and the specific area A is set, the determination unit 218 determines whether the gaze point P of the examinee is present in the specific area A and outputs determination data. In the example illustrated in FIG. 8, since the gaze point P is present outside the specific area A, the determination unit 218 outputs determination data indicating that the gaze point P is not present in the specific area A.

On the other hand, when the gaze point P is present in the specific area A as illustrated in FIG. 9 such as a case in which the gaze point P moves and enters the specific area A, the determination unit 218 outputs determination data indicating that the gaze point P is present in the specific area A.

When the determination data indicating that the gaze point P is present in the specific area A is output from the determination unit 218, the display controller 202 displays the second indicator M2 at a position different from that of the first indicator M1 on the display screen 101S as illustrated in FIG. 9. When the determination data indicating that the gaze point P of the examinee is not present in the specific area A is output from the determination unit 218, the display controller 202 does not display the second indicator M2. It is possible to perform evaluation with high certainty by displaying the second indicator M2 only when the examinee certainly gazes at the first indicator M1.

In the present embodiment, whether or not there is a visual field deficiency is evaluated as a visual function of the examinee by causing the examinee to gaze at the first indicator M1 displayed on the display screen 101S, then displaying the second indicator M2 at a position different from the first indicator M1, and then determining whether the examinee has recognized the second indicator M2 with the peripheral vision.

Figure 10:
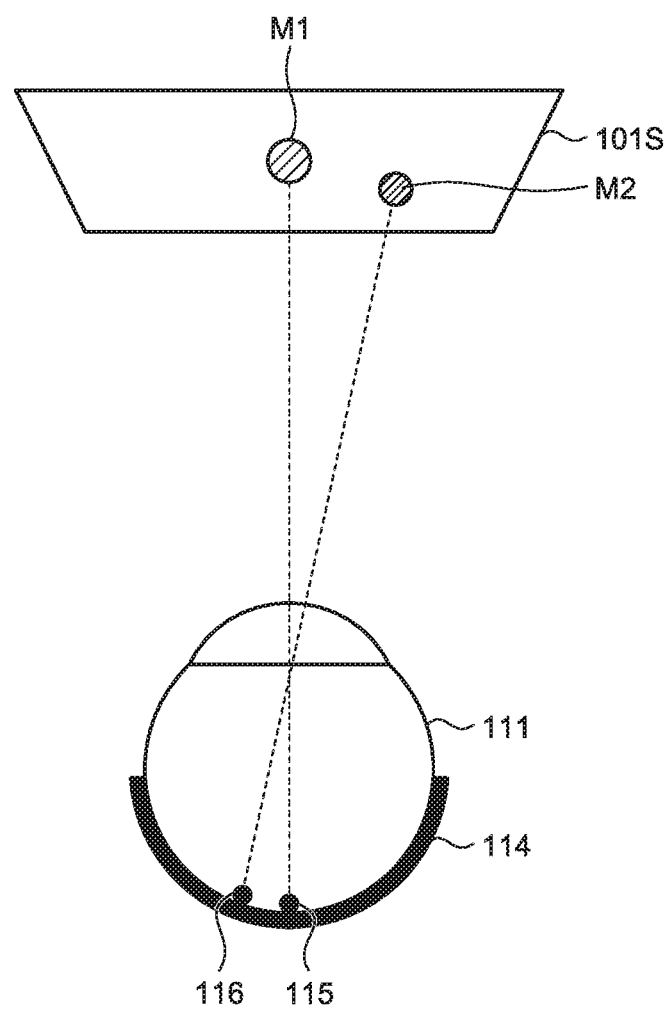
FIG. 10 is a diagram schematically illustrating a principle of an evaluation method according to the embodiment.

FIG. 10 is a diagram schematically illustrating the principle of the evaluation method according to the present embodiment. When the gaze point P of the examinee is present at the first indicator M1 as illustrated in FIG. 10, an image of the first indicator M1 appears at a center of vision 115 of a retina 114. At this time, an image of the second indicator M2 appears in peripheral vision 116 of the retina 114. That is, the examinee watches the second indicator M2 with the peripheral vision 116. Accordingly, the examinee who cannot recognize the second indicator M2 while gazing at the first indicator M1 can be evaluated to have a deficiency of the peripheral vision 116 of the retina 114.

For example, when the examinee has recognized the second indicator M2 while gazing at the first indicator M1, the examinee is caused to push a button of the examinee input unit 70. Accordingly, when an input signal from the examinee input unit 70 has been detected, the arithmetic unit 220 determines that the examinee has recognized the second indicator M2. When the input signal from the examinee input unit 70 has not been detected, the arithmetic unit 220 determines that the examinee has not recognized the second indicator M2.

Figure 11:
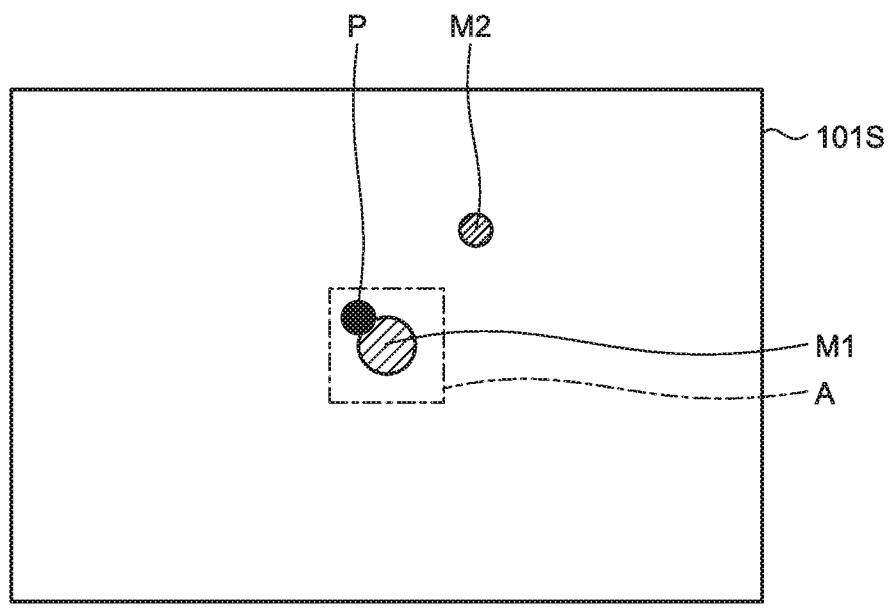
FIG. 11 is a diagram illustrating an example in which a second indicator is displayed at a changed position on the display screen.
Figure 12:
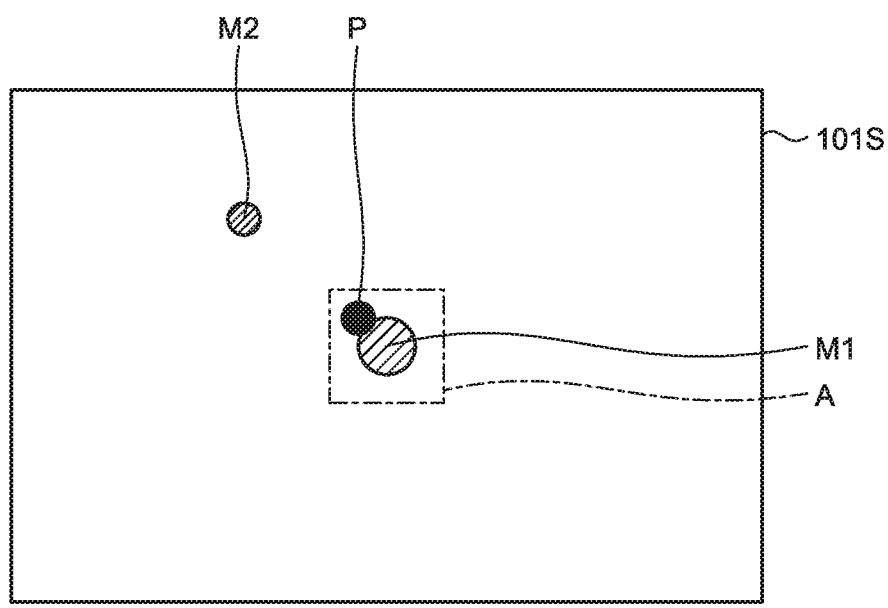
FIG. 12 is a diagram illustrating an example in which the second indicator is displayed at a changed position on the display screen.
Figure 13:
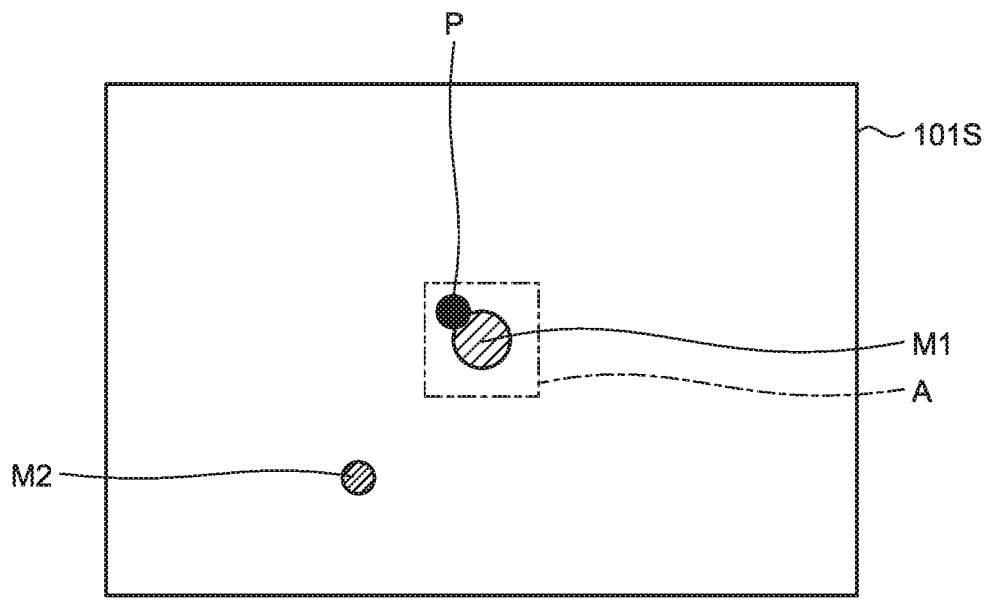
FIG. 13 is a diagram illustrating an example in which the second indicator is displayed at a changed position on the display screen.

This examination is performed multiple times while changing the display position of the second indicator M2. FIGS. 11 to 14 are diagrams illustrating examples in which the second indicator M2 is displayed on the display screen 101S while changing the position thereof. The second indicator M2 is displayed at a lower-right position of the first indicator M1 in FIG. 9, and the second indicator M2 is displayed at an upper-right position of first indicator M1 in FIG. 11. In FIG. 12, the second indicator M2 is displayed at an upper-left position of the first indicator M1. In FIG. 13, the second indicator M2 is displayed at a lower-left position of the first indicator M1. The positions of the second indicator M2 which are illustrated in FIGS. 11 to 13 are examples and the second indicator M2 may be displayed at other positions.

By displaying the second indicator M2 while changing the position thereof in this way and causing the examinee to confirm whether the examinee has recognized the second indicator M2, it is possible to efficiently evaluate whether or not there is a deficiency of the peripheral vision 116 of the retina 114.

At this time, for example, it is conceivable that the examinee intends to recognize the second indicator M2 with the central vision and moves the gaze point P toward the second indicator M2. Further, it is also conceivable that the examinee moves the gaze point P for changing the vision to recognize the second indicator M2 when the examinee has not recognized the second indicator M2. When the examinee moves the gaze point P in this way, it is difficult to perform accurate evaluation.

Figure 14:
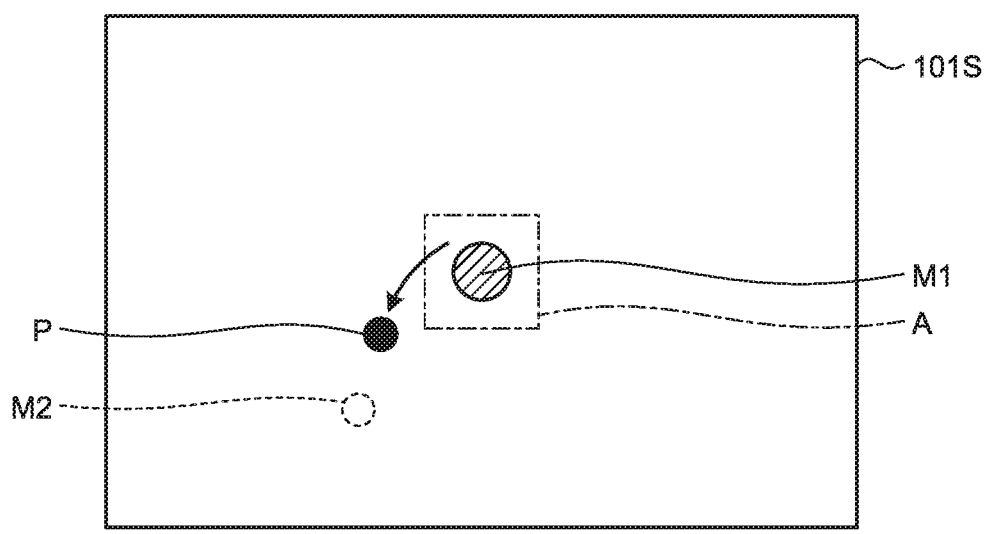
FIG. 14 is a diagram illustrating an example in which the second indicator is displayed at a changed position on the display screen.

Therefore, the determination unit 218 determines whether the gaze point P of the examinee is present in the specific area A continuously after the second indicator M2 has been displayed. For example, when it is determined that the gaze point P of the examinee is not present in the specific area A after the second indicator M2 has been displayed as illustrated in FIG. 14, the display controller 202 does not display the second indicator M2. In this way, by displaying the second indicator M2 only when the examinee certainly gazes at the first indicator M1, it is possible to perform evaluation with high certainty.

Figure 15:
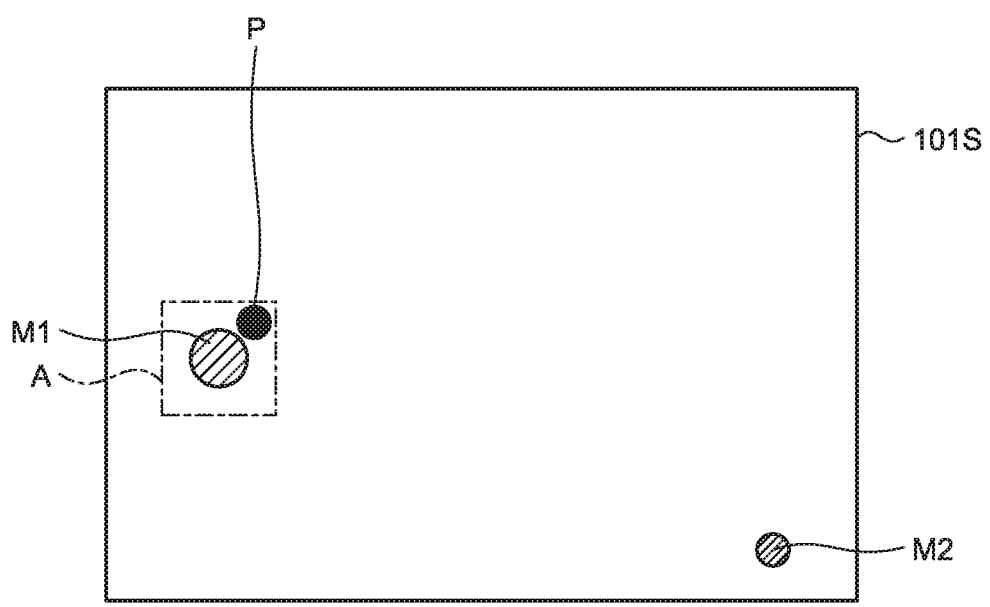
FIG. 15 is a diagram illustrating another example in which the indicators are displayed on the display screen.

The display controller 202 is not limited to displaying the first indicator M1 at the central portion of the display screen 101S and may display the first indicator M1 at another position. FIG. 15 is a diagram illustrating another example in which the indicators are displayed on the display screen 101S. As illustrated in FIG. 15, the display controller 202 may display the first indicator M1, for example, to be close to an end of the display screen 101S (the left end in the drawing). By displaying the first indicator M1 to be close to the end of the display screen 101S in this way, the right area of the first indicator M1 on the display screen 101S can be secured to be greater in comparison with a case in which the first indicator M1 is displayed at the central portion. Accordingly, by displaying the second indicator M2 at the opposite corner of the display screen 101S (the right end in the drawing), whether there is a deficiency of the peripheral vision 116 of the retina 114 can be evaluated in a wide range. The display controller 202 may display the first indicator M1 at any position on the display screen 101S.

Figure 16:
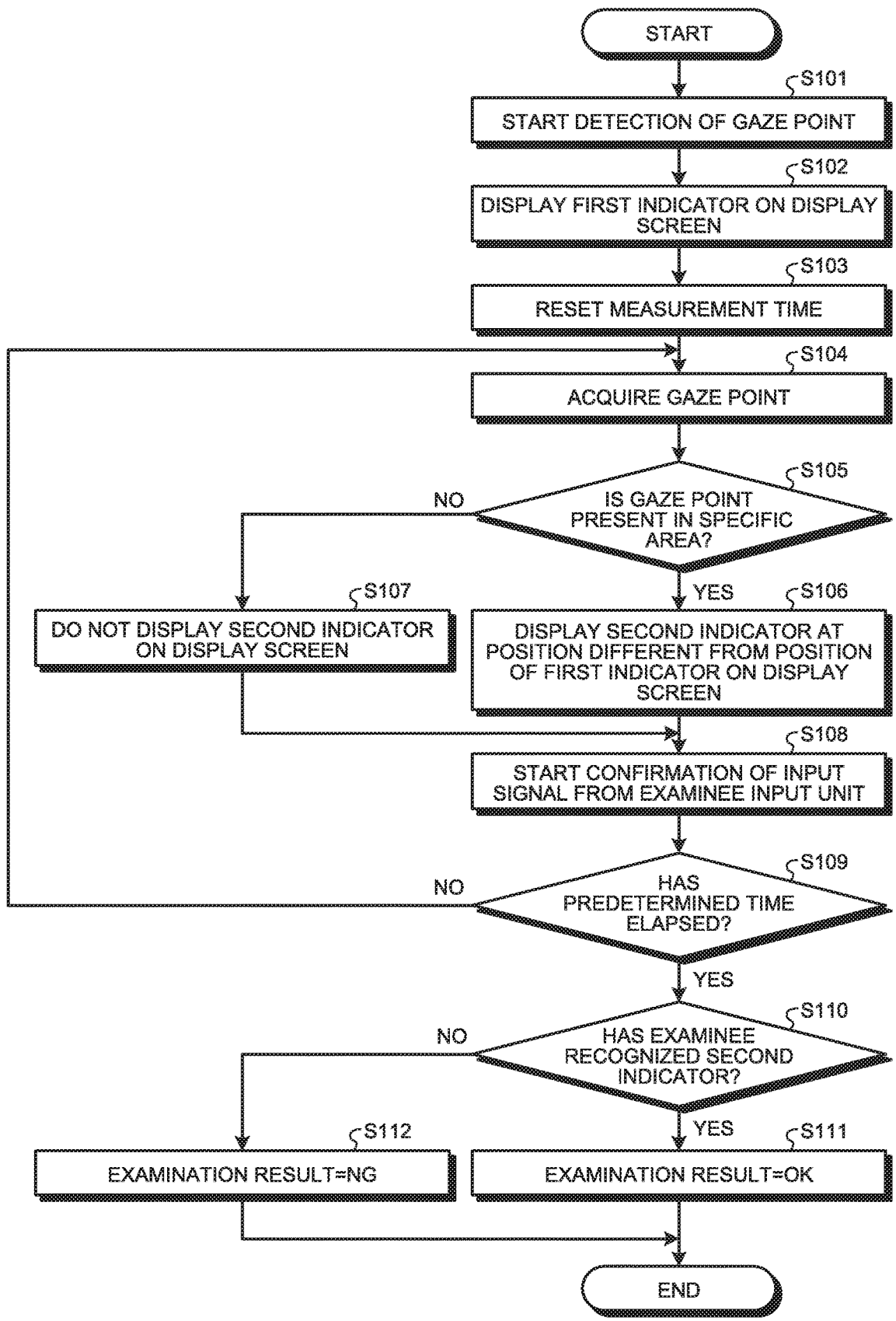
FIG. 16 is a flowchart illustrating an example of a process of determining whether or not an examinee can recognize a second indicator.

FIG. 16 is a flowchart illustrating an example of a process of determining whether the examinee has recognized the second indicator M2. As illustrated in FIG. 16, the gaze point detection unit 214 starts detection of the gaze point P of the examinee (Step S101). After the gaze point P of the examinee has been detected, the display controller 202 displays the first indicator M1 on the display screen 101S (Step S102). In Step S102, the display controller 202 may display the first indicator M1 at any position on the display screen 101S. When the first indicator M1 is displayed on the display screen 101S, the area setting unit 216 sets the specific area A corresponding to the first indicator M1.

When the first indicator M1 is displayed on the display screen 101S, the arithmetic unit 220 resets a measurement time of the timer (Step S103). Thereafter, the gaze point detection unit 214 acquires the gaze point P of the examinee (Step S104). The determination unit 218 determines whether the acquired gaze point P of the examinee is present in the specific area A (Step S105).

When the determination unit 218 determines that the gaze point P is present in the specific area A (Yes in Step S105), the display controller 202 displays the second indicator M2 at a position different from the position of the first indicator M1 on the display screen 101S (Step S106). When the determination unit 218 determines that the gaze point P of the examinee is not present in the specific area A (No in Step S105), the display controller 202 does not display the second indicator M2 (Step S107).

The arithmetic unit 220 starts confirmation of the input signal from the examinee input unit 70 (Step S108). Thereafter, the arithmetic unit 220 determines whether the measurement time of the timer is greater than a predetermined time (Step S109). When it is determined that the measurement time is not greater than the predetermined time (No in Step S109), the arithmetic unit 220 returns to the process of Step S104.

When it is determined that the measurement time is greater than the predetermined time (Yes in Step S109), the arithmetic unit 220 determines whether the examinee has recognized the second indicator M2 (Step S110). The determination of Step S110 is performed based on whether or not there is the input signal from the examinee input unit 70. For example, when the input signal from the examinee input unit 70 has been detected, the arithmetic unit 220 determines that the examinee has recognized the second indicator M2. When the input signal from the examinee input unit 70 has not detected, the arithmetic unit 220 determines that the examinee has not recognized the second indicator M2.

When it is determined that the examinee has recognized the second indicator M2 (Yes in Step S110), the arithmetic unit 220 outputs a message indicating that the examination result is normal (Step S111). On the other hand, when it is determined that the examinee has not recognized the second indicator M2 (No in Step S110), the arithmetic unit 220 outputs a message indicating that the examination result is abnormal (Step S112).

Figure 17:
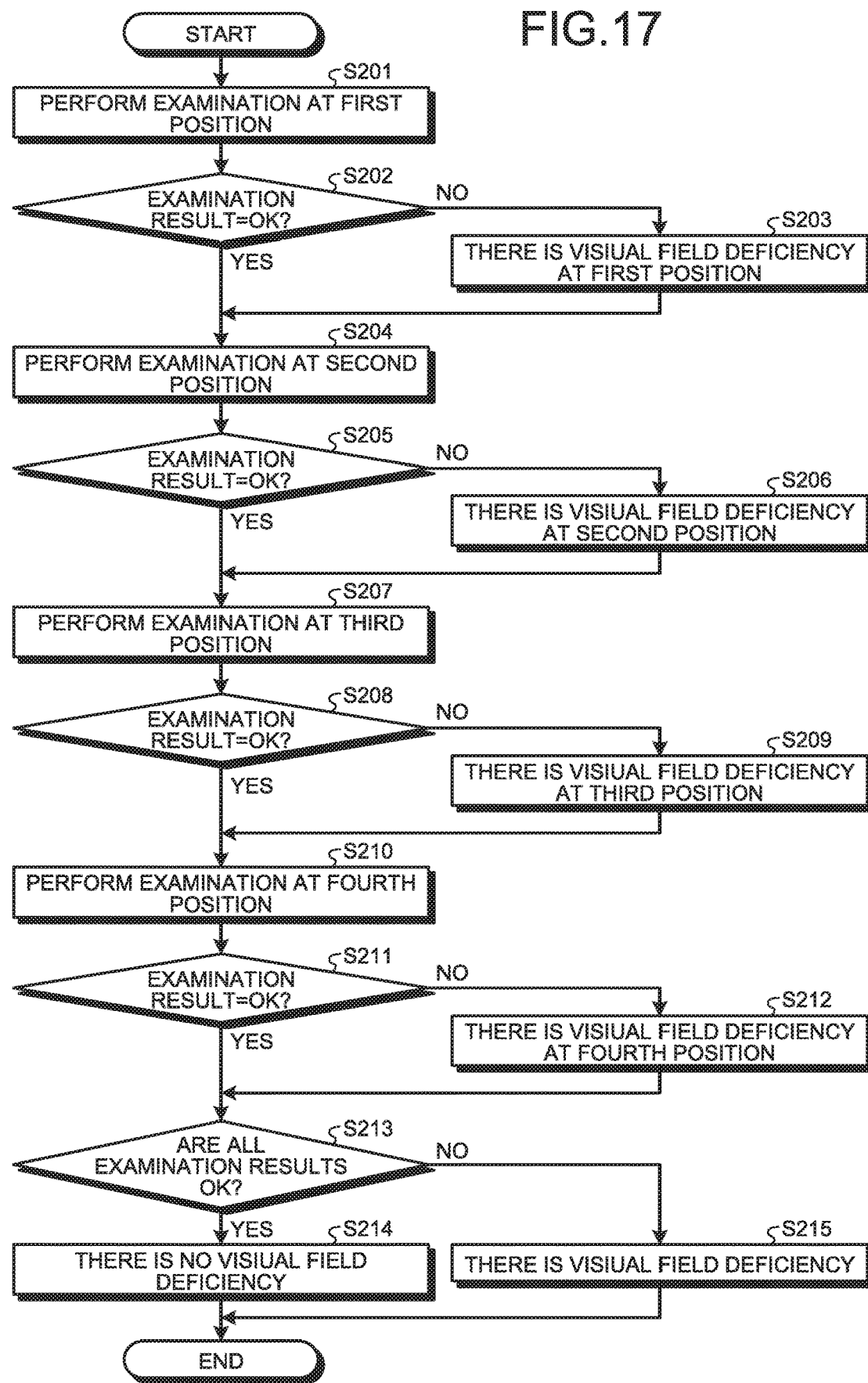
FIG. 17 is a flowchart illustrating an example of the evaluation method according to the embodiment.

FIG. 17 is a flowchart illustrating an example of the evaluation method according to the present embodiment. In the example illustrated in FIG. 17, a case in which the second indicator M2 is displayed at four positions illustrated in FIGS. 9, 11, 12, and 13 will be described. In the following description, it is assumed that the position of the second indicator M2 illustrated in FIG. 9 is a first position, the position of the second indicator M2 illustrated in FIG. 11 is a second position, the position of the second indicator M2 illustrated in FIG. 12 is a third position, and the position of the second indicator M2 illustrated in FIG. 13 is a fourth position.

As illustrated in FIG. 17, first, in the case in which the second indicator M2 is displayed at the first position, it is determined whether the examinee has recognized the second indicator M2 by performing the process illustrated in FIG. 16 (Step S201). Thereafter, the evaluation unit 224 determines whether the examination result output from the arithmetic unit 220 is normal (Step S202).

When the output result from the arithmetic unit 220 is normal (Yes in Step S202), the evaluation unit 224 performs the subsequent step. When the output result from the arithmetic unit 220 is abnormal (No in Step S202), the evaluation unit 224 determines that there is a visual field deficiency at the first position, stores the determination result in the storage 222 (Step S203), and performs the subsequent step.

After Step S202 or S203, in the case in which the second indicator M2 is displayed at the second position, it is determined whether the examinee has recognized the second indicator M2 by performing the process illustrated in FIG. 16 (Step S204). Thereafter, the evaluation unit 224 determines whether the examination result output from the arithmetic unit 220 is normal (Step S205).

When the output result from the arithmetic unit 220 is normal (Yes in Step S205), the evaluation unit 224 performs the subsequent step. When the output result from the arithmetic unit 220 is abnormal (No in Step S205), the evaluation unit 224 determines that there is a visual field deficiency at the second position, stores the determination result in the storage unit 222 (Step S206), and performs the subsequent step.

After Step S205 or S206, in the case in which the second indicator M2 is displayed at the third position, it is determined whether the examinee has recognized the second indicator M2 by performing the process illustrated in FIG. 16 (Step S207). Thereafter, the evaluation unit 224 determines whether the examination result output from the arithmetic unit 220 is normal (Step S208).

When the output result from the arithmetic unit 220 is normal (Yes in Step S208), the evaluation unit 224 performs the subsequent step. When the output result from the arithmetic unit 220 is abnormal (No in Step S208), the evaluation unit 224 determines that there is a visual field deficiency at the third position, stores the determination result in the storage unit 222 (Step S209), and performs the subsequent step.

After Step S208 or S209, in the case in which the second indicator M2 is displayed at the fourth position, it is determined whether the examinee has recognized the second indicator M2 by performing the process illustrated in FIG. 16 (Step S210). Thereafter, the evaluation unit 224 determines whether the examination result output from the arithmetic unit 220 is normal (Step S211).

When the output result from the arithmetic unit 220 is normal (Yes in Step S211), the evaluation unit 224 performs the subsequent step. When the output result from the arithmetic unit 220 is abnormal (No in Step S211), the evaluation unit 224 determines that there is a visual field deficiency at the fourth position, stores the determination result in the storage unit 222 (Step S212), and performs the subsequent step.

After Step S211 or S212, the evaluation unit 224 determines whether all the examination results are normal (Step S213). When it is determined that all the examination results are normal (Yes in Step S213), the evaluation unit 224 outputs an evaluation result indicating that there is no visual field deficiency (Step S214). When at least one of the examination results is abnormal (No in Step S213), the evaluation unit 224 outputs an evaluation result indicating that the examinee has a visual field deficiency (Step S215). In Step S215, the evaluation unit 224 may evaluate at which position there is a visual field deficiency based on the determination results stored in the storage unit 222.

As described above, the line-of-sight detecting device 100 according to the present embodiment includes: a display screen 101S configured to display images; a gaze point detection unit 214 configured to detect a position of a gaze point P of an examinee who observes the display screen 101S; an area setting unit 216 configured to set a specific area A in an area corresponding to a first indicator M1 which is displayed or disposed on the display screen 101S; a determination unit 218 configured to determine whether the gaze point P is present in the specific area A based on a detection result of the position of the gaze point P; a display controller 202 configured to display a second indicator M2 at a position different from the first indicator M1 on the display screen 101S when the determination unit 218 determines that the gaze point P is present in the specific area A; a arithmetic unit 220 configured to determine whether the examinee has recognized the second indicator M2; and an evaluation unit 224 configured to evaluate a visual function of the examinee based on a determination result from the arithmetic unit 220, wherein the display controller 202 is further configured not to display the second indicator M2 when the determination unit 218 determines that the gaze point P is not present in the specific area A after the second indicator M2 has been displayed on the display screen 101S.

The evaluation method according to the present embodiment includes: detecting a position of a gaze point P of an examinee who observes a display screen 101S that displays an image; setting a specific area A in an area corresponding to a first indicator M1 which is displayed or disposed on the display screen 101S; determining whether the gaze point P is present in the specific area A based on a detection result of the position of the gaze point P; displaying a second indicator M2 at a position different from the first indicator M1 on the display screen 101S when determining that the gaze point P is present in the specific area A; determining whether the examinee has recognized the second indicator M2; evaluating a visual function of the examinee based on a determination result of the recognition of the second indicator; and not displaying the second indicator M2 when determining that the gaze point P is not present in the specific area A after the second indicator M2 has been displayed on the display screen S101.

The non-transitory storage medium that stores the evaluation program according to the present embodiment causes a computer to perform: detecting a position of a gaze point P of an examinee who observes a display screen S101 that displays an image; setting a specific area A in an area corresponding to a first indicator M1 which is displayed or disposed on the display screen 101S; determining whether the gaze point P is present in the specific area A based on a detection result of the position of the gaze point P; displaying a second indicator M2 at a position different from the first indicator M1 on the display screen 101S when determining that the gaze point P is present in the specific area A; determining whether the examinee has recognized the second indicator M2; evaluating a visual function of the examinee based on a determination result of the recognition of the second indicator; and not displaying the second indicator M2 when determining that the gaze point P is not present in the specific area A after the second indicator M2 has been displayed on the display screen 101S.

According to this configuration, when the determination unit 218 determines that the gaze point P is present in the specific area A, the second indicator M2 is displayed at a position different from the first indicator M1 on the display screen 101S and thus it is possible to display the second indicator M2 only when the examinee certainly gazes at the first indicator M1. Accordingly, it is possible to perform evaluation with high accuracy.

In the line-of-sight detecting device 100 according to the present embodiment, the display controller 202 does not display the second indicator M2 when the determination unit 218 determines that the gaze point P is not present in the specific area A after the second indicator M2 has been displayed on the display screen 101S. Accordingly, by displaying the second indicator M2 only when the examinee certainly gazes at the first indicator M1, it is possible to perform evaluation with high certainty.

The line-of-sight detecting device 100 according to the present embodiment further includes the examinee input unit 70 to which a recognition state of the second indicator M2 by the examinee is input, and the arithmetic unit 220 determines whether the examinee has recognized the second indicator M2 based on the input result to the examinee input unit 70. Accordingly, it is possible to easily perform valuation with high accuracy.

The technical scope of the application is not limited to the above-mentioned embodiment and can be appropriately modified without departing from the gist of the application. For example, in the above-mentioned embodiment, the first indicator M1 is displayed on the display screen 101S, but the application is not limited thereto. For example, the first indicator M1 may be disposed at a predetermined position on the display screen 101S.

In the above-mentioned embodiment, the display controller 202 does not display the second indicator M2 when the determination unit 218 determines that the gaze point P is not present in the specific area A after the second indicator M2 has been displayed on the display screen 101S, but the application is not limited thereto. For example, when the determination unit 218 determines that the gaze point P is not present in the specific area A after the second indicator M2 has been displayed on the display screen 101S, the evaluation unit 224 may keep the second indicator M2 displayed and invalidate the evaluation of the visual function. Accordingly, it is possible to perform evaluate with high certainty. When the determination unit 218 determines that the gaze point P is not present in the specific area A after the second indicator M2 has been displayed on the display screen 101S, for example, the display controller 202 may perform display for calling the examinee's attention. For example, when an output device that outputs voice, vibration, or an optical signal is provided, the output controller 226 may output voice, vibration, an optical signal, or the like from the output device in addition to or instead of the display for calling the examinee's attention.

According to the application, it is possible to provide an evaluation device, an evaluation method, and a non-transitory storage medium that can perform evaluation with higher accuracy.

Although the application has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. An evaluation device comprising:
   a display screen configured to display images;
   a gaze point detection unit configured to detect a position of a gaze point of an examinee who observes the display screen;
   an area setting unit configured to set a specific area as an area surrounding a first indicator which is displayed or disposed on the display screen;
   a determination unit configured to determine whether the gaze point is present in the specific area based on a detection result of the position of the gaze point;
   a display controller configured to display a second indicator at a position which is positioned outside of the specific area and which is different from a position of the first indicator on the display screen when the determination unit determines that the gaze point is present in the specific area;
   an arithmetic unit configured to determine whether the examinee has recognized the second indicator; and an evaluation unit configured to evaluate a visual function of the examinee based on a determination result from the arithmetic unit, wherein the display controller is further configured not to display the second indicator when the determination unit determines that the gaze point is not present in the specific area after the second indicator has been displayed on the display screen, and the specific area is an area in which it is determined whether the examinee is gazing at the first indicator.

2. The evaluation device according to claim 1, further comprising an examinee input unit to which a recognition state of the second indicator by the examinee is input, wherein the arithmetic unit determines whether the examinee has recognized the second indicator based on an input result to the examinee input unit.

3. An evaluation method comprising:

detecting a position of a gaze point of an examinee who observes a display screen that displays an image;

setting a specific area as an area surrounding a first indicator which is displayed or disposed on the display screen;

determining whether the gaze point is present in the specific area based on a detection result of the position of the gaze point;

displaying a second indicator at a position which is positioned outside of the specific area and which is different from a position of the first indicator on the display screen when determining that the gaze point is present in the specific area;

determining whether the examinee has recognized the second indicator;

evaluating a visual function of the examinee based on a determination result of the recognition of the second indicator, and not displaying the second indicator in response to determining that the gaze point is not present in the specific area after the second indicator has been displayed on the display screen, wherein the specific area is an area in which it is determined whether the examinee is gazing at the first indicator.

4. A non-transitory storage medium that stores an evaluation program causing a computer to perform:

detecting a position of a gaze point of an examinee who observes a display screen that displays an image;

setting a specific area as an area surrounding a first indicator which is displayed or disposed on the display screen;

determining whether the gaze point is present in the specific area based on a detection result of the position of the gaze point;

displaying a second indicator at a position which is positioned outside of the specific area and which is different from a position of the first indicator on the display screen when determining that the gaze point is present in the specific area;

determining whether the examinee has recognized the second indicator;

evaluating a visual function of the examinee based on a determination result of the recognition of the second indicator, and not displaying the second indicator in response to determining that the gaze point is not present in the specific area after the second indicator has been displayed on the display screen, wherein the specific area is an area in which it is determined whether the examinee is gazing at the first indicator.

* * * * *